United States Patent
Zhu et al.

(10) Patent No.: US 11,643,378 B2
(45) Date of Patent: May 9, 2023

(54) PROPANE SEPARATION WITH COMPRESSOR REBOILER

(71) Applicant: UOP LLC, Des Plaines, IL (US)

(72) Inventors: Xin X Zhu, Long Grove, IL (US); Stephen T. King, Villa Park, IL (US); Glen John Pomorski, Park Ridge, IL (US); Joseph Edward Zimmerman, Arlington Heights, IL (US)

(73) Assignee: UOP LLC

( * ) Notice: Subject to any disclaimer, the term of this patent is extended or adjusted under 35 U.S.C. 154(b) by 0 days.

(21) Appl. No.: 17/670,243

(22) Filed: Feb. 11, 2022

(65) Prior Publication Data

US 2022/0315510 A1  Oct. 6, 2022

Related U.S. Application Data

(60) Provisional application No. 63/169,434, filed on Apr. 1, 2021.

(51) Int. Cl.
| | |
|---|---|
| *C07C 7/09* | (2006.01) |
| *C07C 7/04* | (2006.01) |
| *B01D 3/14* | (2006.01) |
| *B01D 1/28* | (2006.01) |
| *B01D 3/32* | (2006.01) |
| *C07C 7/00* | (2006.01) |

(52) U.S. Cl.
CPC .................. *C07C 7/09* (2013.01); *B01D 1/28* (2013.01); *B01D 3/148* (2013.01); *B01D 3/322* (2013.01); *C07C 7/005* (2013.01); *C07C 7/04* (2013.01)

(58) Field of Classification Search
CPC .. C07C 7/09; C07C 7/005; C07C 7/04; B01D 1/28; B01D 3/148; B01D 3/322
See application file for complete search history.

(56) References Cited

U.S. PATENT DOCUMENTS

| | | | |
|---|---|---|---|
| 4,753,667 A * | 6/1988 | O'Connell | ................ C07C 7/04 62/620 |
| 7,981,256 B2 | 7/2011 | Wegerer | |
| 10,315,971 B2 | 6/2019 | King | |
| 10,633,305 B2 | 4/2020 | Zhao et al. | |
| 10,859,313 B2 | 12/2020 | Zhao et al. | |
| 2008/0141712 A1* | 6/2008 | Verma | ................... F25J 3/0242 62/620 |
| 2008/0302650 A1 | 12/2008 | Bello | |
| 2009/0120780 A1* | 5/2009 | Wegerer | .................. B01D 3/14 202/158 |

(Continued)

OTHER PUBLICATIONS

"Search Report and Written Opinion for H222450-WO", dated Jul. 18, 2022.

*Primary Examiner* — Ali Z Fadhel
(74) *Attorney, Agent, or Firm* — Paschall & Associates, LLC; James C. Paschall (57) ABSTRACT

A process and apparatus reboil a propylene splitter bottoms by heat exchange and/or a deethanizer bottoms stream with a compressed propylene splitter overhead stream. Use of single splitter compressor and operation of the propane-propylene splitter column at lower pressure are enabled, whereas conventionally two splitter compressors and higher splitter pressure were necessary to provide a propylene product stream and a propane recycle stream of equivalent quality.

18 Claims, 1 Drawing Sheet

(56) References Cited

U.S. PATENT DOCUMENTS

| | | | |
|---|---|---|---|
| 2012/0000244 A1* | 1/2012 | Sechrist | B01D 3/007 |
| | | | 62/620 |
| 2013/0131417 A1* | 5/2013 | Werba | C07C 5/321 |
| | | | 585/500 |
| 2018/0185766 A1* | 7/2018 | King | C07C 7/04 |
| 2020/0109893 A1 | 4/2020 | Ducote, Jr. et al. | |

\* cited by examiner

The FIGURE is a schematic representation of the process and apparatus of the present disclosure.

PROPANE SEPARATION WITH COMPRESSOR REBOILER

CROSS-REFERENCE TO RELATED APPLICATIONS

This application claims priority from U.S. Provisional Application No. 63/169,434, filed Apr. 1, 2021, which is incorporated herein in its entirety.

FIELD

The field relates to separation of hydrogen and light hydrocarbons at cryogenic temperatures. More particularly, the field relates to propylene recovery from light hydrocarbons.

BACKGROUND

Dehydrogenation of hydrocarbons is an important commercial hydrocarbon conversion process because of the existing and growing demand for dehydrogenated hydrocarbons for the manufacture of various chemical products such as detergents, high octane gasolines, oxygenated gasoline blending components, pharmaceutical products, plastics, synthetic rubbers, and other products which are well known to those skilled in the art. In particular, demand of propylene in the petrochemical industry has grown substantially due to its use as a precursor in the production of polypropylene for packaging materials and other commercial products. Other downstream uses of propylene include the manufacture of acrylonitrile, acrylic acid, acrolein, propylene oxide and glycols, plasticizer oxo alcohols, cumene, isopropyl alcohol, and acetone. One route for producing propylene is the dehydrogenation of propane.

A process for the conversion of paraffins to olefins involves passing a paraffin feed stream over a highly selective catalyst, where the paraffin is dehydrogenated to the corresponding olefin producing a dehydrogenation reactor effluent. Cooling and separation of the dehydrogenation reactor effluent into a hydrocarbon-rich fraction and a hydrogen-rich vapor fraction, part of which is non-recycled net gas, is provided in a cryogenic separation system that requires refrigeration for cooling the process streams in order to separate hydrogen from light hydrocarbon liquid. The conventional cryogenic separation system cools process streams alone to remove hydrogen from light hydrocarbon. However, further fractionation is needed to separate the C2− material from the C3 hydrocarbons in the dehydrogenation effluent in a deethanizer column which also typically requires a refrigeration package.

Improvements in cryogenic separation systems are necessary to render propylene production and purification more economical.

SUMMARY

We have discovered an improved process and apparatus that reboil a propylene-propane splitter bottoms stream by heat exchange with a compressed propylene splitter overhead stream and/or a deethanizer bottoms stream.

These and other features, aspects, and advantages of the present disclosure are further explained by the following detailed description, drawing and appended claims.

Definitions

Figure 1:
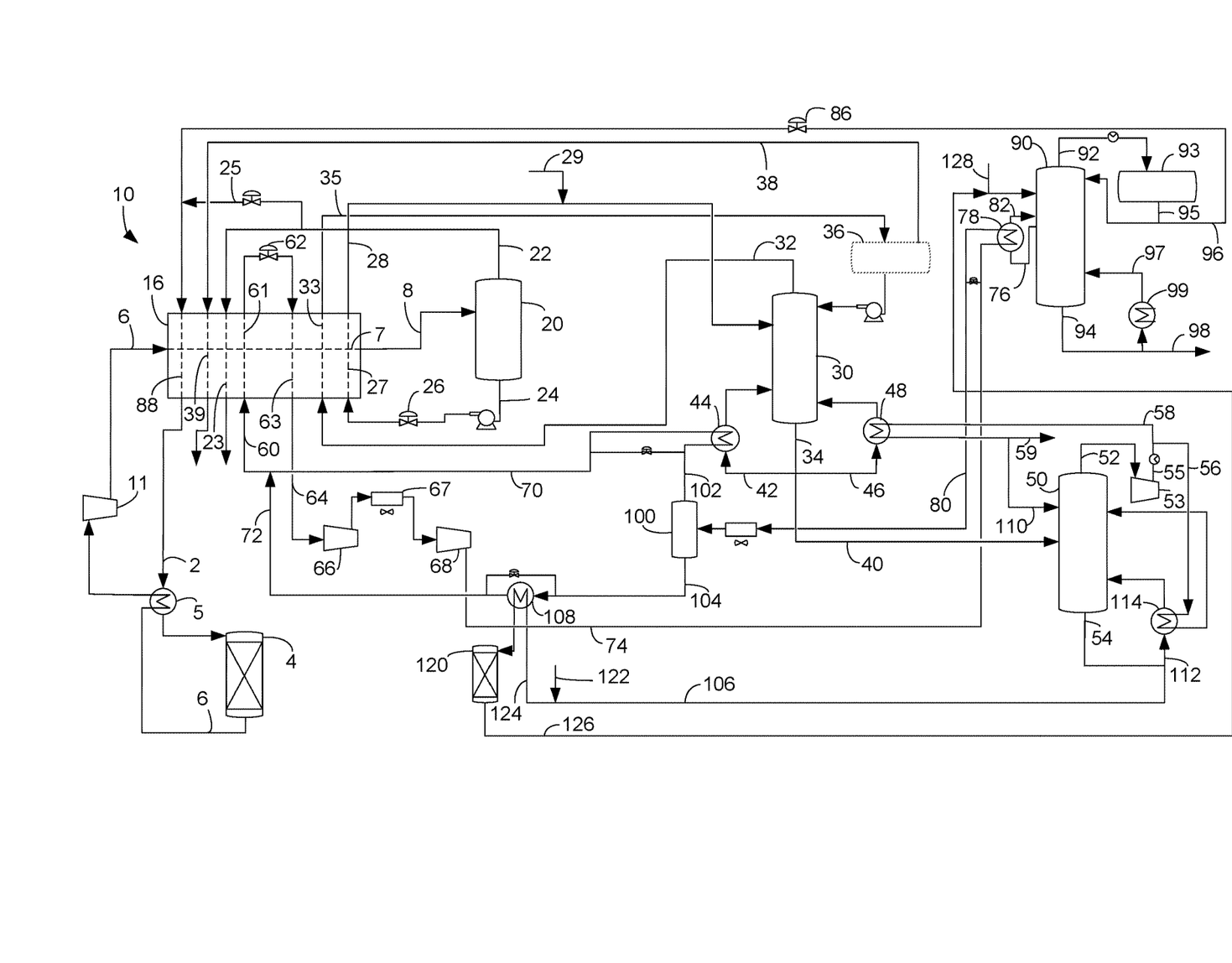
The FIGURE is a schematic representation of the process and apparatus of the present disclosure.

The following detailed description is merely exemplary in nature and is not intended to limit the application and uses of the embodiment described. Furthermore, there is no intention to be bound by any theory presented in the preceding background or the following detailed description.

The term "communication" means that material flow is operatively permitted between enumerated components.

The term "downstream communication" means that at least a portion of material flowing to the subject in downstream communication may operatively flow from the object with which it communicates.

The term "upstream communication" means that at least a portion of the material flowing from the subject in upstream communication may operatively flow to the object with which it communicates.

The term "direct communication" means that flow from the upstream component enters the downstream component without undergoing a compositional change due to physical fractionation or chemical conversion.

The term "bypass" means that the object is out of downstream communication with a bypassing subject at least to the extent of bypassing.

As used herein, the term "separator" means a vessel which has an inlet and at least an overhead vapor outlet and a bottoms liquid outlet and may also have an aqueous stream outlet from a boot. A flash drum is a type of separator which may be in downstream communication with a separator that may be operated at higher pressure.

As used herein, the term "predominant" or "predominate" means greater than 50%, suitably greater than 75% and preferably greater than 90%.

The term "$C_x$" is to be understood to refer to molecules having the number of carbon atoms represented by the subscript "x". Similarly, the term "$C_x-$" refers to molecules that contain less than or equal to x and preferably x and less carbon atoms. The term "$C_x+$" refers to molecules with more than or equal to x and preferably x and more carbon atoms.

The term "column" means a distillation column or columns for separating one or more components of different volatilities. Unless otherwise indicated, each column includes a condenser on an overhead of the column to condense and reflux a portion of an overhead stream back to the top of the column and a reboiler at a bottom of the column to vaporize and send a portion of a bottom stream back to the bottom of the column. Feeds to the columns may be preheated. The top pressure is the pressure of the overhead vapor at the outlet of the column. The bottom temperature is the liquid bottom outlet temperature. Unless otherwise indicated, overhead lines and bottom lines refer to the net lines from the column downstream of the reflux or reboil to the column. Alternatively, a stripping stream may be used for heat input near the bottom of the column.

As used herein, the term "a component-rich stream" means that the rich stream coming out of a vessel has a greater concentration of the component than the feed to the vessel.

As used herein, the term "a component-lean stream" means that the lean stream coming out of a vessel has a smaller concentration of the component than the feed to the vessel.

DETAILED DESCRIPTION

The disclosure is a process and apparatus in which an overhead of a propane-propylene splitter column is compressed in a first stage heat pump with the heat of compression being used to reboil the propane-propylene splitter column. By heat exchange with the splitter bottoms liquid, the overhead vapor condenses. When this condensed liquid is returned to the lower operating pressure of the column, the stream partially flashes, reducing temperature and enabling the stream to be used as reflux. Conventionally, either the operating pressure of the propane-propylene splitter column is set to allow for the condensation of the net overhead vapor using air or water cooling, or the heat pump has two stages of compression, with the discharge pressure of the second stage set to enable condensation of the net overhead vapor by air or water cooling. In an additional embodiment, the process and apparatus enable the excess compressed overhead stream, not condensed in the splitter reboiler, to be condensed in a deethanizer reboiler and the heat removed being used to heat the deethanizer column. In this embodiment, the need for operating the splitter column at an elevated pressure is eliminated thus saving capital cost and/or eliminating the need for a second stage of compression for the second stage heat pump.

The process and apparatus comprise passing a reactor feed stream comprising hydrocarbons and hydrogen in a reactor feed line 2 to a dehydrogenation reactor 4 to provide a dehydrogenation reactor effluent stream in an effluent line 6. The reactor feed stream in line 2 may be pre-heated in a hot combined feed exchanger 5 before it passes to the dehydrogenation reactor 4.

The reactor feed stream comprises propane. In some embodiments, the reactor feed stream comprises other light paraffins such as ethane, butane, normal butane, isobutane, pentane or iso-pentane. In some embodiments, the reactor feed stream comprises at least one paraffin having 2 to 30 carbon atoms. The hydrogen-to-hydrocarbon molar ratio of the feed stream is in a range of 0.005 to 0.6.

The pre-heated reactor feed stream is contacted with a dehydrogenation catalyst in the dehydrogenation reactor 4 maintained at dehydrogenation conditions to produce a dehydrogenation reactor effluent stream comprising hydrogen, unconverted paraffins, and olefins in an effluent line 6. The dehydrogenation reactor 4 may be a reaction zone that includes multi-stages or multiple reactors, often in series.

The dehydrogenation catalyst may be a highly selective platinum-based catalyst system. One example of a suitable catalyst for a light paraffin dehydrogenation process may be a catalyst composite comprising a Group VIII noble metal component, a Group IA or IIA metal component, and a component selected from the group consisting of tin, germanium, lead, indium, gallium, thallium, or mixtures thereof, all on an alumina support.

Dehydrogenation conditions include a temperature of from about 400° to about 900° C., a pressure of from about 0.01 to about 10 atmospheres absolute, and a liquid hourly space velocity (LHSV) of from about 0.1 to about 100 $hr^{-1}$. Generally, for normal paraffins, the lower the molecular weight, the higher the temperature required for comparable conversion. The pressure in the dehydrogenation reactor 4 is maintained as low as practicable, consistent with equipment limitations, to maximize the chemical equilibrium advantages. The dehydrogenation reaction is typically endothermic.

The reactor feed stream in the reactor feed line 2 may be heat exchanged with the reactor effluent stream in line 6 in the hot combined feed exchanger 5. The dehydrogenation reactor effluent stream in line 6 is cooled by heat exchange with the reactor feed stream 2 in the hot combined feed exchanger 5 and compressed in a reactor effluent compressor 11 to provide a compressed reactor effluent stream. The compressed reactor effluent stream in the reactor effluent line 6 is passed to a cryogenic separation system 10 to provide an olefin stream and a hydrogen stream.

The reactor effluent stream may comprise light hydrocarbons and hydrogen. In paraffin dehydrogenation, the desired product is often propylene which must be separated from other light hydrocarbons such as propane and hydrogen. Propane can be recycled to the dehydrogenation reactor 4 for propylene production. Hydrogen is a valuable byproduct and may be used elsewhere in the refinery such as for fuel for fired heaters of a dihydrogen process. Some hydrogen may be recycled back to the reactors 4 to control the dehydrogenation reaction.

To separate the hydrogen from the light hydrocarbons effectively, the reactor effluent stream is cooled by passing it to a cryogenic heat exchanger 16 to condense the hydrocarbons. In the cryogenic heat exchanger 16, the reactor effluent stream in line 6 is routed through an effluent pass 7 in which it is cooled by heat exchange with other streams passing through the cryogenic heat exchanger to provide a cooled reactor effluent stream in line 8.

A single-stage separator 20 is in downstream communication with the effluent pass 7. The cooled reactor effluent stream in line 8 is separated in a single-stage separator 20 to provide a net gas overhead stream rich in hydrogen in a separator overhead line 22 extending from an overhead of the single-stage separator and a separator bottoms stream rich in hydrocarbons in a separator bottoms line 24 extending from a bottom of single-stage the separator. The single-stage separator 20 may operate at a temperature between about −150° C. (−101° F.) and about 66° C. (150° F.) and more commonly between about −95° C. (−138° F.) and about −40° C. (−40° F.), and a gauge pressure between about 690 kPa (100 psig) and about 1.4 MPa (200 psig).

The net gas overhead stream in the separator overhead line 22 is sufficiently hydrogen pure from one stage of separation by the thorough condensation of the hydrocarbons in the single-stage separator 20. The net gas overhead stream may possess a hydrogen purity of at least 94 mol %, suitably at least 95 mol %, preferably at least 96 mol % and most preferably at least 96.5 mol % molecular hydrogen. A hydrogen recycle line 25 may recycle through a control valve thereon a portion of the net gas in the separator overhead line 22 to a reactor feed stream in line 6 to provide hydrogen requirements for the reaction. The net gas overhead stream can be routed to the cryogenic heat exchanger 16 to be heated by passing it through a separator overhead pass 23 and provide a product hydrogen stream that can be used elsewhere in the refinery or plant. The separator overhead pass 23 may be in direct downstream communication with the separator overhead line 22 of the single-stage separator 20. The warmed off-gas stream may be provided at a temperature of about 32° C. (90° F.) to about 60° C. (140° F.) and a gauge pressure of about 760 kPa (110 psig) to about 1.2 MPa (170 psig).

The separator bottoms stream is rich in hydrocarbons that can be refined for valuable products. The separator bottoms stream in the separator bottoms line 24 may be pumped and expanded over an expander 26 to vaporize the hydrocarbons and be passed through the cryogenic exchanger 16. The vaporized hydrocarbons are cooled by giving up the heat of vaporization and therefore assist in cooling the reactor effluent stream passed through the cryogenic exchanger in the effluent pass 7 from line 6. The separator bottoms stream is heated by passing it through a deethanizer feed pass 27 in the cryogenic heat exchanger 16 to provide a deethanizer feed stream in a deethanizer feed line 28.

The deethanizer feed stream in line 28 comprises ethane and propane which must be separated from each other. Hence, the deethanizer feed stream in line 28 at a temperature between about −31° C. (−25° F.) and about −3° C. (25° F.) is passed to a deethanizer column 30 for fractionation. An optional polypropylene plant recycle stream in line 29 comprising light ends may be added to the deethanizer feed stream in line 28. The deethanizer column 30 separates the deethanizer feed stream in the deethanizer feed line 28 into a deethanizer overhead stream in a deethanizer overhead line 32 extending from an overhead of the deethanizer column which is rich in ethane and a deethanized bottoms stream in a deethanizer bottoms line 34 extending from a bottom of the deethanizer column which is rich in propane. The deethanized overhead stream in line 32 is transported to the cryogenic heat exchanger 16 and passed through a deethanizer overhead pass 33 in the cryogenic heat exchanger to be cooled to further condense C3+ hydrocarbons and provide a cooled deethanizer overhead stream in a cooled deethanizer overhead line 35. The deethanizer overhead pass 33 may be in downstream communication with the deethanizer overhead line 32 of the deethanizer column 30.

The cooled deethanizer overhead stream in line 35 is returned to a deethanizer receiver 36. The deethanizer receiver 36 is a separator that separates gas from condensate. The deethanizer receiver 36 may be in downstream communication with the deethanizer overhead pass 33 in the cryogenic heat exchanger 16. The deethanizer receiver operates at a temperature of about −32° C. (−25° F.) to about −60° C. (−75° F.) and a gauge pressure of about 690 kPa (100 psig) to about 1.1 MPa (160 psig). A deethanized off-gas stream in a deethanizer receiver overhead line 38 extending from an overhead of the deethanizer receiver 36 carries the off-gas stream which is rich in C2− hydrocarbons to the cryogenic heat exchanger 16. The off-gas stream in line 38 is heated by heat exchange in an off-gas pass 39 through the cryogenic heat exchanger 16 to provide a warmed off-gas stream. The warmed off gas stream may be provided at a temperature of about −32° C. (90° F.) to about 60° C. (140° F.) and a gauge pressure of about 690 kPa (100 psig) to about 1.1 MPa (160 psig).

The deethanized bottoms stream in the deethanizer bottoms line 34 which is rich in C3+ hydrocarbons may extend from a bottom of the deethanizer column and be split into two or three streams. A net deethanized bottoms stream may be taken as a splitter feed stream in a net deethanizer bottoms line 40 from the deethanized bottoms stream in line 34. The splitter feed stream comprising propylene and propane may be transported in the net deethanizer bottoms line 40 to a propylene—propane splitter column 50. The propylene—propane splitter column 50 may be in downstream communication with the deethanizer bottoms line 34. A first reboil deethanized bottom stream may be taken in a first reboil deethanized bottoms line 42 from the deethanized bottoms stream in line 34 and passed through a first side of a first deethanizer reboiler heat exchanger 44, boiled up by heat exchange with a hot refrigerant on a second side of the first deethanizer reboil heat exchanger and returned to a lower end of the deethanizer column 30. The first side of the first deethanizer reboil heat exchanger 44 may be in downstream communication with the deethanizer bottoms line 34. The second side of the first deethanizer reboil heat exchanger may be in downstream communication with a refrigerant separator overhead line 102 and/or a first refrigerant compressor 66 and perhaps a second compressor 68 and/or a second refrigerant pass 63 through the cryogenic heat exchanger 16 all to be described hereinafter.

In an embodiment, a second reboil deethanized bottom stream may be taken in a second reboil deethanized bottoms line 46 from the deethanized bottoms stream in line 34 and passed through a first side of a second deethanizer reboil heat exchanger 48, boiled up by heat exchange with a second compressed splitter overhead stream in a second splitter overhead line 58 to be described hereinafter in a second side of the second deethanizer reboil heat exchanger and returned to a lower end of the deethanizer column 30. The first side of the second deethanizer reboil exchanger 48 may be in downstream communication with the deethanizer bottoms line 34 and a second side of the deethanizer reboil exchanger may be in downstream communication with a splitter compressor 53. The deethanizer bottoms may operate at a temperature of about 16° C. (50° F.) to about 43° C. (120° F.) and a gauge pressure of no more than about 1.7 MPa (250 psig) preferably between about 690 kPa (100 psig) to about 1.4 MPa (200 psig).

A refrigerant stream transported in a refrigerant line 70 from the second side of the first deethanizer reboil heat exchanger 44 may be mixed with a liquid refrigerant stream in line 72 and be cooled in the cryogenic heat exchanger 16. The cryogenic heat exchanger 16 operates with a refrigerant stream that may comprise a mixed refrigerant stream comprising nitrogen and some or all of C1 to C5 hydrocarbons. The refrigerant stream is passed by a combined refrigerant line 60 through a first refrigerant pass 61 in the cryogenic heat exchanger 16. In line 60 before the first refrigerant pass, the refrigerant may be at a temperature of about 16° C. (60° F.) to about 43° C. (110° F.) and a gauge pressure of about 3.3 MPa (485 psig) to about 3.9 MPa (565 psig). In the first refrigerant pass 61, the refrigerant stream is cooled by heat exchange with other streams in the cryogenic heat exchanger 16 and exits the cryogenic heat exchanger. The first refrigerant pass 61 of the combined refrigerant line 60 in the cryogenic heat exchanger 16 may be in downstream communication with the second side of the first deethanizer reboil exchanger 44. The cooled refrigerant stream is expanded and vaporized in the refrigerant expander 62 cooling it to provide a cold refrigerant stream at a temperature of about −67° C. (−90° F.) to about −101° C. (−150° F.) and a gauge pressure of about 310 kPa (45 psig) to about 1 MPa (140 psig). The cold refrigerant stream is passed in the cryogenic heat exchanger 16 through a second refrigerant pass 63 to cool all the other streams passing through the cryogenic heat exchanger while heating the cold refrigerant stream. The second refrigerant pass 63 of the combined refrigerant line 60 in the cryogenic heat exchanger 16 may be in downstream communication with the refrigerant expander 62. The warmed refrigerant stream may be at a temperature of about 10° C. (50° F.) to about 54° C. (130° F.) and a gauge pressure of about 276 kPa (40 psig) to about 931 kPa (135 psig) when it exits the cryogenic heat exchanger after the second refrigerant pass 63 in a warmed refrigerant line 64.

The warmed refrigerant stream exiting the cryogenic heat exchanger 16 in line 64 from the second refrigerant pass 63 is at low pressure and vaporous. Hence, it is subjected to compression to boost its pressure. The warmed refrigerant stream in line 64 may be compressed by a first refrigerant compressor 66 and perhaps by a second refrigerant compressor 68 to provide a compressed refrigerant stream in a compressed refrigerant line 74. An air cooler 67 may be installed to cool compressed refrigerant between the first refrigerant compressor 66 and the second refrigerant compressor 68. Knock-out drums that are not shown may be provided upstream of each compressor to remove liquids from the compressor inlets. The compressed refrigerant stream in line 74 may be at a temperature of about 107° C. (225° F.) to about 152° C. (275° F.) and a gauge pressure of about 4.5 MPa (650 psig) to about 5.2 MPa (750 psig).

To cool the compressed refrigerant stream in line 74 it may be heat exchanged with a depropanizer side stream in a depropanizer side line 76 in a depropanizer upper reboiler heat exchanger 78 to provide a cooled compressed refrigerant stream in a cooled compressed refrigerant line 80 and a heated depropanizer side stream in a depropanizer return line 82. The depropanizer upper reboiler heat exchanger 78 has a first side in communication with the depropanizer side line 76 from a depropanizer column 90 and a second side in communication with the compressed refrigerant line 74. The second side of said depropanizer upper reboiler heat exchanger is in downstream communication with the first refrigerant compressor 66 and/or the second refrigerant compressor 68. A valved bypass is provided on the compressed refrigerant line 74 to the cooled compressed refrigerant line 80 to regulate the amount of heating across the upper depropanizer reboiler heat exchanger 78.

The cooled compressed refrigerant stream in the cooled compressed refrigerant line 80 may be further cooled in an air cooler and passed to a refrigerant separator 100 to be separated into a vapor refrigerant stream in an overhead refrigerant line 102 extending from an overhead of the refrigerant separator and a liquid refrigerant stream in a bottoms refrigerant line 104 extending from a bottom of the refrigerant separator. The refrigerant separator 100 may be in downstream communication with a second side of the depropanizer upper reboiler heat exchanger 78. The vapor refrigerant stream in the overhead refrigerant line 102 may be further cooled by passing it through the second side of the first deethanizer reboil heat exchanger 44 for heat exchange with the first reboil deethanized bottom stream in line 42 passed through the first side of the first deethanizer reboil heat exchanger 44. The second side of the first deethanizer reboil heat exchanger 44 may be in downstream communication with the refrigerant separator overhead line 102. A condensed refrigerant stream is transported in the condensed refrigerant line 70 from the first deethanizer reboil exchanger 44 back to reconstitute the combined refrigerant stream in the combined refrigerant line 60 to restart the cycle. A valved bypass is provided on the overhead refrigerant line 102 to regulate the amount of heat exchange across the first deethanizer reboiler heat exchanger 44. The refrigerant stream is compressed in compressors 66 and perhaps 68 before heat exchange in the first deethanizer reboil exchanger 44 with the deethanized bottoms stream in line 42 to provide sufficient heat for reboiling.

The liquid refrigerant stream in the bottoms refrigerant line 104 also has heat that can be recovered. The liquid refrigerant stream in line 104 may be heat exchanged with a combined net splitter bottoms stream to heat the combined net splitter bottoms stream in a combined net splitter bottoms line 124 in a selective hydrogenation feed exchanger 108. A first side of the selective hydrogenation feed exchanger 108 may be in downstream communication with the net splitter bottoms line 106 and a second side may be in downstream communication with the refrigerant separator bottoms line 104. A valved bypass is provided on the bottoms refrigerant line 104 to regulate the amount of heat exchange across the selective hydrogenation feed exchanger 108. The cooled liquid refrigerant stream in a liquid refrigerant line 72 is transported from the selective hydrogenation feed exchanger 108 back to reconstitute the combined refrigerant stream in line 60 with the condensed refrigerant stream in line 70 to restart the refrigeration cycle. Cooling of the refrigerant stream in the combined refrigerant line 60 is conducted in the cryogenic heat exchanger 16 after heat exchange with the first deethanized reboil bottoms stream in the first deethanizer reboiler heat exchanger 44.

The splitter feed stream in line 40 comprises propane and propylene that must be separated to obtain the propylene product and recycle propane to the reactor 4. The propylene— propane splitter column 50 fractionates the splitter feed stream into a splitter overhead stream rich in propylene in a splitter overhead line 52 extending from an overhead of the splitter column and a splitter bottoms stream rich in propane in a splitter bottoms line 54 extending from a bottom of the splitter column. The splitter overhead stream is compressed in a splitter compressor 53 which serves to condense the splitter overhead stream and provide a compressed splitter overhead stream in a compressed splitter line 55. The splitter compressor 53 may be in downstream communication with the splitter overhead line 52. The compressed splitter overhead stream in line 55 may be further cooled by a cooling water heat exchanger. The compressed splitter overhead stream in line 55 may exhibit a temperature of about 48° C. (80° F.) to about 71° C. (160° F.) and a gauge pressure of about 1.2 MPa (175 psig) to about 1.9 MPa (275 psig). After heat exchange the temperature of the compressed splitter overhead stream may be reduced by about 3° C. (5° F.) to about 6° C. (10° F.).

A first compressed splitter overhead stream in a first compressed splitter overhead line 56 is taken from the compressed splitter overhead stream in line 55. A second compressed splitter overhead stream in a second compressed splitter overhead line 58 is taken from the compressed splitter overhead stream in line 55. The second deethanized bottoms stream in the second deethanized bottoms line 46 is reboiled by heat exchange with said second compressed splitter overhead stream in line 58 in the second deethanizer reboil heat exchanger 48. A first side of the second deethanizer reboil heat exchanger 48 may be in downstream communication with the deethanizer bottoms line 34 and a second side of the second deethanizer reboil heat exchanger 48 may be in downstream communication with the splitter compressor 53. The heat exchange in the second deethanizer reboil heat exchanger 48 serves to cool the second compressed splitter overhead stream in line 58. A propylene product stream in line 59 may be taken from the cooled second compressed splitter overhead stream, and a second reflux splitter overhead stream in a second reflux splitter line 110 may be refluxed as a second reflux stream to the propylene splitter column 50 at compression pressure.

A reboil splitter bottoms stream is taken in a reboil splitter bottoms line 112 from the splitter bottoms stream in the splitter bottoms line 54 and reboiled by heat exchange with the first compressed splitter overhead stream in the first compressed splitter bottoms line 56 in a splitter reboil heat exchanger 114. The splitter reboil heat exchanger 114 has a first side in downstream communication with the splitter bottoms line 54 and a second side in downstream communication with the splitter compressor 53. The first compressed splitter overhead stream in the first compressed splitter bottoms line 56 cooled by heat exchange with the reboil splitter bottoms stream in line 112 in the splitter reboil heat exchanger 114 is returned as a first reflux stream to the splitter column 50 at compression pressure. The splitter bottoms stream in line 54 may exhibit a temperature of about 21° C. (70° F.) to about 32° C. (90° F.) and a gauge pressure of about 62 kPa (90 psig) to about 1034 kPa (150 psig).

A net splitter bottoms stream is taken in the net splitter bottoms line 106 from the splitter bottoms stream. The net splitter bottoms stream is rich in propane and may be recycled to the reactor 4. However, diolefins and acetylenes may injure the dehydrogenation catalyst and should be converted to monoolefins in a selective hydrogenation reactor 120. Accordingly, hydrogen from a hydrogen stream 122 is added to the net splitter bottoms stream to provide a combined net splitter bottoms stream in line 124 that is heated in the selective hydrogenation feed heat exchanger 108. The combined net splitter bottoms stream in the combined net splitter bottoms line 124 may be heat exchanged in the selective hydrogenation feed heat exchanger 108 with the liquid refrigerant stream in the bottoms refrigerant line 104 and charged to the selective hydrogenation reactor 120.

The combined net splitter bottoms stream is selectively hydrogenated in the presence of hydrogen and a selective hydrogenation catalyst in the selective hydrogenation reactor 120. The selective hydrogenation reactor 120 is normally operated at relatively mild hydrogenation conditions. These conditions will normally result in the hydrocarbons being present as liquid phase materials, so reactants will normally be maintained under the minimum pressure sufficient to maintain the reactants as liquid phase hydrocarbons. A broad range of suitable operating gauge pressures therefore extends from about 276 kPa (40 psig) to about 5516 kPa (800 psig) or about 345 kPa (50 psig) to about 2069 kPa (300 psig). A relatively moderate temperature between about 25° C. (77° F.) and about 350° C. (662° F.), or between about 50° C. (122° F.) and about 200° C. (392° F.) is typically employed. The liquid hourly space velocity of the reactants through the selective hydrogenation catalyst should be above about 1.0 $hr^{-1}$ and about 35.0 $hr^{-1}$. To avoid the undesired saturation of a significant amount of monoolefinic hydrocarbons, the mole ratio of hydrogen to diolefinic hydrocarbons in the combined net splitter bottoms stream entering the bed of selective hydrogenation catalyst is maintained between 0.75:1 and 1.8:1. Any suitable catalyst which is capable of selectively hydrogenating diolefins may be used. Suitable catalysts include, but are not limited to, a catalyst comprising copper and at least one other metal such as titanium, vanadium, chrome, manganese, cobalt, nickel, zinc, molybdenum, and cadmium or mixtures thereof. The metals are preferably supported on inorganic oxide supports such as silica and alumina, for example.

A selectively hydrogenated net splitter bottom stream comprising propane is transported in a hydrogenated effluent line 126 perhaps after gas separation and added to a fresh propane feed stream in line 128 and both are fed to the depropanizer column 90. The depropanizer column 90 may be in downstream communication with the splitter bottoms line 54. The depropanizer column 90 separates the selectively hydrogenated net splitter bottoms stream and the fresh propane feed stream to provide a depropanizer overhead stream rich in propane in an overhead line 92 extending from an overhead of the depropanizer column and a depropanized bottoms stream rich in C4+ hydrocarbons in a depropanizer bottoms line 94 extending from a bottom of the depropanizer column.

The depropanizer overhead stream in the depropanizer overhead line 92 is cooled and may be fully condensed and fed to a depropanizer receiver 93. A receiver bottoms stream exits the bottom of the depropanizer receiver in a depropanizer receiver bottoms line 95. A depropanizer reflux stream taken from the depropanizer receiver bottoms line 95 refluxes condensed propane back to the depropanizer column 90. The depropanizer receiver 93 operates at a temperature of about 20° C. (68° F.) to about 70° C. (158° F.) and a gauge pressure of about 1.4 MPa (200 psig) to about 1.8 MPa (261 psig).

A depropanizer net overhead stream in a net depropanizer overhead line 96 is expanded across a depropanizer overhead expander 86 to vaporize and cool it, supplemented with hydrogen from the hydrogen recycle line 25, and further cooled in a reactor feed pass 88 in the cryogenic heat exchanger 16 to provide the reactor feed stream in the reactor feed line 2. The hydrogen-to-hydrocarbon molar ratio of the reactor feed stream in the range of 0.005 to 0.6 is controlled by the control valve on the hydrogen recycle line 25.

The reactor feed stream in the reactor feed line 2 exiting the reactor feed pass 88 may be provided at a temperature of about 32° C. (90° F.) to about 60° C. (140° F.) and a gauge pressure of about 69 kPa (10 psig) to about 0.5 MPa (80 psig).

A depropanizer side stream taken in a depropanizer side line 76 from the depropanizer 90 may be reboiled in a depropanizer upper reboiler heat exchanger 78 depropanizer by heat exchange with the compressed refrigerant stream in line 74 to provide a cooled compressed refrigerant stream in line 80 and a heated depropanizer side stream in line 82, which is returned to the depropanizer column 90 through its side as a vapor stream. The depropanizer side stream taken in line 76 is suitably a liquid stream taken from a liquid trap in the depropanizer column 90.

The depropanizer bottoms stream in the depropanizer bottoms line 94 is rich in C4+ hydrocarbons. A depropanizer reboil stream taken in line 97 from the depropanizer bottoms stream in line 94 may be heated in a depropanizer reboil heat exchanger 99 and returned to a lower end of the depropanizer column 90. A net depropanizer bottoms stream comprising C4+ hydrocarbons may be taken in a net depropanizer bottoms line 98 as product. The depropanizer bottoms 93 operates at a temperature of about 80° C. (176° F.) to about 130° C. (195° F.) and a gauge pressure of about 1.5 MPa (217 psig) to about 2 MPa (290 psig).

The process and apparatus enable use of single splitter compressor 53 and operation of the propylene splitter column 50 at lower pressure, whereas conventionally two splitter compressors and higher splitter column pressure was necessary to provide propylene product stream and propane recycle stream of high quality.

SPECIFIC EMBODIMENTS

While the following is described in conjunction with specific embodiments, it will be understood that this description is intended to illustrate and not limit the scope of the preceding description and the appended claims.

A first embodiment of the disclosure is a process for separating propane from propylene comprising passing a splitter feed stream comprising propane and propylene to a propylene splitter column to provide a splitter overhead stream rich in propylene and a splitter bottoms stream rich in propane; compressing the splitter overhead stream to provide a compressed splitter overhead stream; reboiling the splitter bottoms stream by heat exchange with the compressed splitter overhead stream. An embodiment of the disclosure is one, any or all of prior embodiments in this paragraph up through the first embodiment in this paragraph, further comprising taking a first compressed splitter overhead stream from the compressed splitter overhead stream and reboiling the splitter bottoms stream by heat exchange with the first compressed splitter overhead stream and taking a second compressed splitter overhead stream from the compressed splitter overhead stream and reboiling a deethanized bottoms stream by heat exchange with the second splitter overhead stream. An embodiment of the disclosure is one, any or all of prior embodiments in this paragraph up through the first embodiment in this paragraph, further comprising passing a deethanizer feed stream comprising ethane and propane to the deethanizer column to provide a deethanizer overhead stream rich in ethane and a deethanized bottoms stream rich in propane; taking a reboil deethanized bottoms stream from the deethanized bottom stream and heat exchanging the reboil deethanized bottoms stream with the second compressed splitter overhead stream; and taking a net deethanized bottoms stream as the splitter feed stream. An embodiment of the disclosure is one, any or all of prior embodiments in this paragraph up through the first embodiment in this paragraph further comprising taking a propylene product stream from the compressed splitter overhead stream and returning the compressed splitter overhead stream to the propylene splitter column at compression pressure. An embodiment of the disclosure is one, any or all of prior embodiments in this paragraph up through the first embodiment in this paragraph further comprising taking a reboil splitter bottoms stream from the splitter bottoms stream and reboiling the reboil splitter bottoms stream by heat exchange with the compressed splitter overhead stream and taking a net splitter bottoms stream from the splitter bottoms stream and passing the net splitter bottoms stream comprising propane to a depropanizer column to provide a depropanizer overhead stream rich in propane and a depropanized bottoms stream rich in C4 hydrocarbons. An embodiment of the disclosure is one, any or all of prior embodiments in this paragraph up through the first embodiment in this paragraph further comprising heating a depropanizer side stream by heat exchange with a compressed refrigerant stream to provide a cooled refrigerant stream. An embodiment of the disclosure is one, any or all of prior embodiments in this paragraph up through the first embodiment in this paragraph further comprising separating the cooled refrigerant in a refrigerant separator into a vapor refrigerant stream in an overhead refrigerant line and liquid refrigerant stream in a bottoms refrigerant line. An embodiment of the disclosure is one, any or all of prior embodiments in this paragraph up through the first embodiment in this paragraph wherein the reboil deethanized bottoms stream taken from the deethanized bottom stream and heat exchanged with the second compressed splitter overhead stream is a second reboil deethanized bottoms stream and further comprising taking a first reboil deethanized bottoms stream from the deethanized bottoms stream and heat exchanging the first reboil deethanized bottoms stream by heat exchange with the vapor refrigerant stream. An embodiment of the disclosure is one, any or all of prior embodiments in this paragraph up through the first embodiment in this paragraph further comprising heating the net splitter bottoms stream by heat exchange with the liquid refrigerant stream and selectively hydrogenating the net splitter bottoms stream in the presence of hydrogen and selective hydrogenation catalyst before passing the net splitter bottoms stream comprising propane to a depropanizer column.

A second embodiment of the disclosure is an apparatus for separating propylene from propane comprising a propylene splitter column comprising splitter overhead line extending from an overhead of the propylene splitter column and a splitter bottoms line extending from a bottom of the propylene splitter column; a splitter compressor in downstream communication with the splitter overhead line; a splitter reboil heat exchanger with a first side in downstream communication with the splitter bottoms line and a second side in downstream communication with the splitter compressor. An embodiment of the disclosure is one, any or all of prior embodiments in this paragraph up through the second embodiment in this paragraph further comprising a deethanizer column including a deethanizer overhead line extending from an overhead of the deethanizer column and a deethanizer bottoms line extending from a bottom of the deethanizer column and a deethanizer reboil exchanger with a first side in communication with the deethanizer bottoms line and a second side in communication with the splitter compressor. An embodiment of the disclosure is one, any or all of prior embodiments in this paragraph up through the second embodiment in this paragraph wherein the propylene splitter column is in downstream communication with the deethanizer bottoms line. An embodiment of the disclosure is one, any or all of prior embodiments in this paragraph up through the second embodiment in this paragraph further comprising a depropanizer column in downstream communication with the splitter bottoms line. An embodiment of the disclosure is one, any or all of prior embodiments in this paragraph up through the second embodiment in this paragraph wherein the depropanizer column includes an upper reboiler with a first side in communication with a side stream from the depropanizer column and a second side in communication with a refrigerant line. An embodiment of the disclosure is one, any or all of prior embodiments in this paragraph up through the second embodiment in this paragraph further comprising a refrigerant compressor and wherein the second side of the upper reboiler is in downstream communication with the refrigerant compressor. An embodiment of the disclosure is one, any or all of prior embodiments in this paragraph up through the second embodiment in this paragraph further comprising a refrigerant separator including a refrigerant separator overhead line extending from an overhead of the refrigerant separator and a refrigerant separator bottoms line extending from a bottom of the refrigerant separator wherein the refrigerant separator is in downstream communication with the second side of the upper reboiler. An embodiment of the disclosure is one, any or all of prior embodiments in this paragraph up through the second embodiment in this paragraph wherein the deethanizer reboil exchanger is a first deethanizer reboil exchanger and further comprising a second deethanizer reboiler exchanger with a first side in communication with the deethanizer bottoms line and a second side in communication with the refrigerant separator overhead line. An embodiment of the disclosure is one, any or all of prior embodiments in this paragraph up through the second embodiment in this paragraph further comprising a selective hydrogenation feed exchanger with a first side in communication with the splitter bottoms line and a second side in communication with the refrigerant separator bottoms line.

A third embodiment of the disclosure is an apparatus for separating propylene from propane comprising a propylene splitter column comprising splitter overhead line extending from an overhead of the propylene splitter column and a splitter bottoms line extending from a bottom of the propylene splitter column; a splitter compressor in downstream communication with the splitter overhead line; a deethanizer column including a deethanizer overhead line extending from an overhead of the deethanizer column and a deethanizer bottoms line extending from a bottom of the deethanizer column and a deethanizer reboil exchanger with a first side in communication with the deethanizer bottoms line and a second side in communication with the splitter compressor. An embodiment of the disclosure is one, any or all of prior embodiments in this paragraph up through the third embodiment in this paragraph further comprising a splitter reboil heat exchanger with a first side in downstream communication with the splitter bottoms line and a second side in downstream communication with the splitter compressor.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for separating propane from propylene comprising:
    passing a splitter feed stream comprising propane and propylene to a propylene splitter column to provide a splitter overhead stream rich in propylene and a splitter bottoms stream rich in propane;
    compressing said splitter overhead stream to provide a compressed splitter overhead stream;
    taking a first compressed splitter overhead stream from said compressed splitter overhead stream and reboiling said splitter bottoms stream by heat exchange with said first compressed splitter overhead stream; and
    taking a second compressed splitter overhead stream from said compressed splitter overhead stream and reboiling a deethanized bottoms stream by heat exchange with said second compressed splitter overhead stream.

2. The process of claim 1, further comprising passing a deethanizer feed stream comprising ethane and propane to said deethanizer column to provide a deethanizer overhead stream rich in ethane and a deethanized bottoms stream rich in propane; taking a reboil deethanized bottoms stream from said deethanized bottom stream and heat exchanging said reboil deethanized bottoms stream with said second compressed splitter overhead stream; and taking a net deethanized bottoms stream as said splitter feed stream.

3. The process of claim 2 further comprising taking a propylene product stream from said compressed splitter overhead stream and returning the compressed splitter overhead stream to the propylene splitter column at compression pressure.

4. The process of claim 3 further comprising taking a reboil splitter bottoms stream from said splitter bottoms stream and reboiling said reboil splitter bottoms stream by heat exchange with said compressed splitter overhead stream and taking a net splitter bottoms stream from said splitter bottoms stream and passing said net splitter bottoms stream comprising propane to a depropanizer column to provide a depropanizer overhead stream rich in propane and a depropanized bottoms stream rich in C4 hydrocarbons.

5. The process of claim 4 further comprising heating a depropanizer side stream by heat exchange with a compressed refrigerant stream to provide a cooled refrigerant stream.

6. The process of claim 5 further comprising separating said cooled refrigerant in a refrigerant separator into a vapor refrigerant stream in an overhead refrigerant line and liquid refrigerant stream in a bottoms refrigerant line.

7. The process of claim 6 wherein said reboil deethanized bottoms stream taken from said deethanized bottom stream and heat exchanged with said second compressed splitter overhead stream is a second reboil deethanized bottoms stream and further comprising taking a first reboil deethanized bottoms stream from said deethanized bottoms stream and heat exchanging said first reboil deethanized bottoms stream by heat exchange with said vapor refrigerant stream.

8. The process of claim 7 further comprising heating said net splitter bottoms stream by heat exchange with said liquid refrigerant stream and selectively hydrogenating said net splitter bottoms stream in the presence of hydrogen and selective hydrogenation catalyst before passing said net splitter bottoms stream comprising propane to a depropanizer column.

9. An apparatus for separating propylene from propane comprising:
    a propylene splitter column comprising splitter overhead line extending from an overhead of said propylene splitter column and a splitter bottoms line extending from a bottom of said propylene splitter column;
    a splitter compressor in downstream communication with said splitter overhead line;
    a splitter reboil heat exchanger with a first side in downstream communication with said splitter bottoms line and a second side in downstream communication with said splitter compressor;
    a deethanizer column including a deethanizer overhead line extending from an overhead of said deethanizer column and a deethanizer bottoms line extending from a bottom of said deethanizer column; and
    a deethanizer reboil exchanger with a first side in communication with said deethanizer bottoms line and a second side in communication with said splitter compressor.

10. The apparatus of claim 9 wherein said propylene splitter column is in downstream communication with said deethanizer bottoms line.

11. The apparatus of claim 10 further comprising a depropanizer column in downstream communication with said splitter bottoms line.

12. The apparatus of claim 11 wherein said depropanizer column includes an upper reboiler with a first side in communication with a side stream from said depropanizer column and a second side in communication with a refrigerant line.

13. The apparatus of claim 12 further comprising a refrigerant compressor and wherein said second side of said upper reboiler is in downstream communication with said refrigerant compressor.

14. The apparatus of claim 13 further comprising a refrigerant separator including a refrigerant separator overhead line extending from an overhead of said refrigerant separator and a refrigerant separator bottoms line extending from a bottom of said refrigerant separator wherein said refrigerant separator is in downstream communication with said second side of said upper reboiler.

15. The apparatus of claim 14 wherein said deethanizer reboil exchanger is a first deethanizer reboil exchanger and further comprising a second deethanizer reboiler exchanger with a first side in communication with said deethanizer bottoms line and a second side in communication with said refrigerant separator overhead line.

16. The apparatus of claim 15 further comprising a selective hydrogenation feed exchanger with a first side in communication with the splitter bottoms line and a second side in communication with said refrigerant separator bottoms line.

17. An apparatus for separating propylene from propane comprising:
- a propylene splitter column comprising splitter overhead line extending from an overhead of said propylene splitter column and a splitter bottoms line extending from a bottom of said propylene splitter column;
- a splitter compressor in downstream communication with said splitter overhead line;
- a deethanizer column including a deethanizer overhead line extending from an overhead of said deethanizer column and a deethanizer bottoms line extending from a bottom of said deethanizer column and a deethanizer reboil exchanger with a first side in communication with said deethanizer bottoms line and a second side in communication with said splitter compressor.

18. The apparatus of claim 17 further comprising a splitter reboil heat exchanger with a first side in downstream communication with said splitter bottoms line and a second side in downstream communication with said splitter compressor.

* * * * *